United States Patent
Rich

(10) Patent No.: US 7,989,178 B2
(45) Date of Patent: *Aug. 2, 2011

(54) COLONY ASSAY MINIATURIZATION WITH ENUMERATION OUTPUT

(75) Inventor: Ivan N. Rich, Colorado Springs, CO (US)

(73) Assignee: Hemogenix, Inc., Colorado Springs, CO (US)

( * ) Notice: Subject to any disclaimer, the term of this patent is extended or adjusted under 35 U.S.C. 154(b) by 185 days.

This patent is subject to a terminal disclaimer.

(21) Appl. No.: 12/135,021

(22) Filed: Jun. 6, 2008

(65) Prior Publication Data
US 2009/0011446 A1    Jan. 8, 2009

Related U.S. Application Data

(60) Continuation-in-part of application No. 12/049,921, filed on Mar. 17, 2008, now Pat. No. 7,883,861, which is a continuation of application No. 10/645,077, filed on Aug. 21, 2003, now Pat. No. 7,354,730, which is a continuation-in-part of application No. 10/059,521, filed on Jan. 29, 2002, now Pat. No. 7,354,729, application No. 12/135,021, which is a continuation-in-part of application No. 12/049,815, filed on Mar. 17, 2008, now Pat. No. 7,700,354, which is a division of application No. 10/059,521.

(60) Provisional application No. 60/942,966, filed on Jun. 8, 2007, provisional application No. 60/264,796, filed on Jan. 29, 2001.

(51) Int. Cl.
*C12Q 1/66* (2006.01)

(52) U.S. Cl. ....... 435/8; 435/1.2; 435/2; 435/3; 435/7.2; 435/40.51; 435/40.52; 435/372; 435/374; 435/375; 435/376; 435/377; 435/384; 435/385; 435/386; 435/387; 435/388

(58) Field of Classification Search .................. 435/1.2, 435/1.3, 2, 7.2, 8, 40.51, 40.52, 7.23, 7.24, 435/7.92, 374–377, 384–388, 391, 392, 7.25, 435/14, 25, 381; 436/501, 503, 17, 18, 63, 436/64, 147, 813, 522, 66, 67, 177; 422/61
See application file for complete search history.

(56) References Cited

U.S. PATENT DOCUMENTS

| | | | |
|---|---|---|---|
| 5,328,844 A | 7/1994 | Moore | 435/240.31 |
| 5,580,724 A | 12/1996 | Alter | 435/6 |
| 5,641,641 A | 6/1997 | Wood | 435/8 |
| 5,733,541 A | 3/1998 | Taichman et al. | 424/93.1 |

(Continued)

FOREIGN PATENT DOCUMENTS

WO    WO92/13063    8/1992

(Continued)

OTHER PUBLICATIONS

Aardal, N.P., et al., "Circadian variations in mouse bone marrow", *Exp. Hematol.*, 11(9): 792-801 (1983).

(Continued)

*Primary Examiner* — Gailene R Gabel
(74) *Attorney, Agent, or Firm* — Donna E. Becker

(57) ABSTRACT

A system combining a clonogenic differentiation assay with an instrument-based ATP bioluminescence proliferation assay to produce a standardized colony-forming stem and progenitor cell potency assay is provided.

19 Claims, 7 Drawing Sheets

Relationship between the Colony Forming Cell (CFC) Differentiation Assay and the Bioluminescence ATP Proliferation Assay Performed at 14 Days for Human CFC-GEMM

U.S. PATENT DOCUMENTS

| | | | | |
|---|---|---|---|---|
| 5,814,471 | A | 9/1998 | Wood | 435/8 |
| 5,854,010 | A | 12/1998 | Denison et al. | 435/8 |
| 6,440,407 | B1 | 8/2002 | Bauer et al. | 424/85.1 |
| 6,824,973 | B2 | 11/2004 | Tang et al. | 435/4 |
| 7,354,729 | B2* | 4/2008 | Rich | 435/8 |
| 7,354,730 | B2 | 4/2008 | Rich | 435/8 |
| 7,700,354 | B2* | 4/2010 | Rich | 435/375 |
| 2002/0120098 | A1* | 8/2002 | Bell et al. | 530/300 |

FOREIGN PATENT DOCUMENTS

| | | |
|---|---|---|
| WO | WO94/17177 | 8/1994 |
| WO | WO98/08537 | 3/1998 |
| WO | WO98/21313 | 5/1998 |
| WO | WO98/28437 | 7/1998 |
| WO | WO03/004995 | 1/2003 |
| WO | WO04/018996 | 3/2004 |

OTHER PUBLICATIONS

Aardal, N.P., "Circannual variations of circadian periodicity in murine colony-forming cells", *Exp. Hematol.*, 12:61-37 (1984).

Abkowitz, J., et al., "Cyclic hematopoiesis in dogs: Studies of erythroid burst-forming cells confirm an early stem cell defect", *Exp. Hematol.*, 16:941-945 (1988).

Abraham, N.G., "Hematopoietic effects of benzene inhalation assessed by long-term bone marrow culture", *Environ Health Perspect*, 104(Suppl 6):1277-1282 (1996).

Abrahamsen, J.F., et al., "Circadian cell cycle vaiations of erythro- and myelopoiesis in humans", *Eur. J. Haematol.*, 58(5):333-345 (1997). [Abstract Only].

Ballmaier, M., et al., "c-mpl mutations are the cause of congenital amegakaryocytic thrombocytopenia", *Blood*, 97:139-146 (2001).

Baudoux, E., et al., "Circadian and seasonal variations of hematopoiesis in cord blood", *Bone Marrow Transplantation*, 22(Suppl 1):S12 (1998).

Botta, M., et al., "Toxicity on human hemopoietic progenitors of 2'-2'-difluoro-2' deoxycytidine (gemcitabine)", *Anticancer Research*, 18:1037-1042 (1998).

Bradbury, D.A., et al., "Measuremenet of the ADP:ATP ratio in human leukaemic cell lines can be used as an indicator of cell viability, necrosis and apoptosis", *Journal of Immunological Methods*, 240:79-92 (2000).

Bradley, T.R., et al., "The growth of mouse bone marrow cells in vitro", *Aust. J. Exp. Biol. Med. Sci.*, 44:287-300 (1966).

Bradley, T.R., et al., "The effect of oxyen tension on haemopoietic and fibroblast cell proliferation in vitro", *J. Cell. Physiol.*, 97:517-522 (1978).

Bulanova, E.G., et al., "Bioluminescent assay for human lymphocyte blast transformation", *Immunol. Lett.*, 46(1-2):153-155 (1995).

Carulli, G., et al., "Cyclic oscillations of neutrophils, monocytes, and CD8-positive lymphocytes in a healthy subject", *Haematologica*, 85(4):447-448 (2000).

Castello, G., et al., "Azidothymidine and interferon-α in vitro effects on hematopoiesis: Protective in vitro activity of IL-1 and GM-CSF", *Experimental Hematology*, 23:1367-1371 (1995).

Cerruti, A., et al., "Hematotoxicity of 5-fluorouracil-leucovorin in a setting of adjuvant chemotherapy", *Anticancer Research*, 14:2163-2166 (1994).

Clement, M., et al., "Chemopreventive agent resveratrol, a natural product derived from grapes, triggers CD95 signaling-dependent apoptosis in human tumor cells", *Blood*, 92(3):996-1002 (1998).

Corsini, C., et al., "Idarubicinol myelotoxicity: A comparison of in vitro data with clinical outcome in patients treated with high-dose idarubicin", *British Journal of Cancer*, 82(3):524-528 (2000).

Crouch, S.P.M., et al., "The use of ATP bioluminescence as a measure of cell proliferation and cytotoxicity", *Journal of Immunological Methods*, 160:81-88 (1993).

Doz, F., et al., "Experimental basis for increasing the therapeutic index of carboplatin in brain tumor therapy by pretreatment with WR compounds", *Cancer Chemother. Pharmacol.*, 28:308-310 (1991).

Farris, G., et al., "Benzene-induced hematotoxicity and bone marrow compensation in B6C3F1 mice", *Fundamental and Applied Toxicology*, 36:119-129 (1997).

Fujisaki, T., et al., "Rapid differentiation of a rare subset of adult human Lin CD34 CD38 cells stimulated by multiple growth factors in vitro", *Blood*, 94(6):1926-1932 (1999).

Gabbianelli, M., et al., "Multi-level effects of flt3 ligand on human hematopoiesis: Expansion of putative stem cells and proliferation of granulomonocytic progenitors/monocytic precursors", *Blood*, 86(5):1661-1670 (1995).

Ghielmini, M., et al., "Hematotoxicity on human bone marrow—and umbilical cord blood-derived progenitor cells and in vitro therapeutic index of methoxymorpholinyldoxorubicin and its metabolites", *Cancer Chemother. Pharmacol.*, 42:235-240 (1998).

Ghielmini, M., et al., "In vitro schedule-dependency of myelotoxicity and cytotoxicity of Ecteinascidin 743 (ET-743)", *Annals of Oncology*, 9:989-993 (1998).

Ghielmini, M., et al., "Differential toxicity of anticancer drugs on late (GM-CFC) and early (LTC-IC) hemopoietic progenitors in vitro", *Cell Biology and Toxicology*, 15:395-404 (1999).

Gribaldo, L., et al., "Inhibition of CFU-E/BFU-E by 3'-azido-3'-deoxythymidine, chlorpropamide, and protoporphirin IX zinc (II): a comparison between direct exposure of progenitor cells and long-term exposure of bone marrow cultures", *Toxicological Sciences*, 58:96-101 (2000).

Haurie, C., et al., "Hematopoietic dynamics in grey collies", *Experimental Hematology*, 27:1139-1148 (1999).

Hodgson, G.S., et al., "The organization of hemopoietic tissue as inferred from the effects of 5-fluorouracil", *Exp. Hematol.*, 10(1):26-35 (1982).

Hodgson, G.S., et al., "In vitro production of CFU-S and cells with erythropoiesis repopulating ability by 5-fluorouracil treated mouse bone marrow", *International Journal of Cell Cloning*, 1:49-56 (1983).

Hohl, R.J., "Monoterpenes as regulators of malignant cell proliferation", *Adv. Exp. Med. Biol.*, 401:137-146 (1996).

Holt, D.E., et al., "The myelotoxicity of chloramphenicol: in vitro and in vivo studies: I. in vitro effects on cells in culture", *Hum. Exp. Toxicol.*, 16(10):570-576 (1997).

Horowitz, D., et al., "Colorimetric determination of inhibition of hematopoietic progenitor cells in soft agar", *Journal of Immunological Methods*, 244:49-58 (2000).

Iscove, N.N., et al., "Erythroid colony formation in cultures of mouse and human bone marrow: analysis of the requirement for erythropoietin by gel filtration and affinity chromatography on agarose-concanavalin A", *J. Cell. Physiol.*, 83:309-320 (1974).

Katayama, Y., et al., "Replating potential of colony-forming units of granulocytes/macrophages (CFU-GM) expanded ex vivo by stem cell factor, interleukin (IL)-3, IL-6, granulocyte colony-stimulating factor, erythropoietin with or without thrombopoietin", *Int. J. Hematol.*, 68(2):157-168 (1998).

Konwalinka, G., et al., "A miniaturized agar culture system for cloning human erythropoietic progenitor cells", *Exp. Hematol.*, 12:75-79 (1984).

Kravtsov, V., et al., "Use of the microculture kinetic assay of apoptosis to determine chemosensitivities of leukemias", *Blood*, 92(3):968-980 (1998).

Laerum, O.D., et al., "Chronobiological aspects of bone marrow and blood cells", *Prog. Clin. Biol. Res.*, 59C:87-97 (1981).

Laerum, O,D., "Hematopoiesis occurs in rhythms", *Experimental Hematology*, 23:1145-1147 (1995).

Lerza, R., et al., "In vitro toxicity of a 3'-azido-3'-deoxythymidine and hydroxyurea combination on normal myeloid progenitors", *Anticancer Research*, 18:2755-2758 (1998).

Maddens, S., et al., "Kit signaling inhibits the sphingomyelin-ceramide pathway through $PLC_\gamma 1$: Implication in stem cell factor radioprotective effect", *Blood*, 100(4): 1294-1301 (2002).

McLeod, D., et al., "Improved plasma culture system for production of erythrocytic colonies in vitro: Quantitative assay method for CFU-E", *Blood*, 44 (4):517-534 (1974).

Mosmann, T., "Rapid colorimetric assay for cellular growth and survival: Application to proliferation and cytotoxicity assays", *Journal of Immunological Methods*, 65:55-63 (1983).

Noé, G., et al., "A sensitive sandwich ELISA for measuring erythropoietin in human serum", *Br. J. Haematol.*, 80(3):285-292 (1992).

Parchment, R.E., et al., "Predicting hematological toxicity (myelosuppression) of cytotoxic drug therapy from in vitro tests", *Ann. Oncol.*, 9(4):357-364 (1998).

Parchment, R.E., et al., "Roles for in vitro myelotoxicity tests in preclinical drug development and clinical trial planning", *Toxicol. Pathol.*, 21(2):241-250 (1993). [Abstract Only].

Parent-Massin, D., et al., "In vitro study of pesticide hematotoxicity in human and rat progenitors", *Journal of Pharmacological and Toxicological Methods*, 30(4):203-207 (1993).

Ploemacher, R., et al., "Use of limiting-dilution type long-term marrow cultures in frequency analysis of marrow-repopulating and spleen colony-forming hematopoietic stems cells in the mouse", *Blood*, 78(10):2527-2533 (1991).

Pluznik, D.H., et al., "The induction of clones of normal mast cells by a substance from conditioned medium", *Experimental Cell Research*, 43:553-563 (1966).

Pragnell, I.B., et al., "The effect of stem cell proliferation regulators demonstrated with an in vitro assay", *Blood*, 72(1):196-201 (1988).

Prieto, P., "ECVAM's in-house prevalidation/validation studies in the areas of haematotoxicity, reproductive toxicity, metabolism-mediated toxicity and epithelial barrier function", *The Science of the Total Environment*, 247:349-354 (2000).

Rich, I.N., "The effect of 5-fluorouracil on erythropoiesis", *Blood*, 77(6):1164-1170 (1991).

Rich, I.N., et al., "The effect of reduced oxygen tension on colony formation of erythropoietic cells in vitro", *British Journal of Haematology*, 52:579-588 (1982).

Rich, I.N., et al., "Specific enhancement of mouse CFU-E by mouse transferrin", *Br. J. Haematol.*, 49(4):567-573 (1981). [Abstract Only].

Rich, I.N., et al., "HALO—a multifunctional colony-forming based assay platform for drug development and basic and clinical research", Abstracts of the American Society of Hematology 44th annual meeting, *Blood*, 100(11 Pt 1):1a-1016a (2002). [Abstract Only].

Rich, I.N., et al., "Validation and development of a predictive paradigm for hemotoxicology using a multifunctional bioluminescence colony-forming proliferation assay", *Toxicological Sciences*, 87(2): 427-441 (2005).

Rosendaal, M., et al., "Haemopoietic stem cells are organised for use on the basis of their generation-age", *Nature*, 264:68-69 (1976).

Scheving, L., et al., "Circadian variation in cell division of the mouse alimentary tract, bone marrow and corneal epithelium", *Anat. Rec.*, 191:479-486 (1978).

Smith, M, et al., "Biomarkers of leukemia risk: Benzene as a model", *Environmental Health Perspectives*, 106(4): 937-946 (1998).

Snyder, R., et al., "The toxicology of benzene", *Environmental Health Perspectives*, 100:293-306 (1993).

Sottong, P.R., et al., "Measurement of T-Lymphocyte responses in whole-blood cultures using newly synthesized DNA and ATP", *Clinical and Diagnostic Laboratory Immunology*, 7(2): 307-311 (2000).

Stenn, K.S., et al., "What controls hair follicle cycling?", *Exp. Dermatol.*, 8:229-236 (1999).

Wood, P., et al., "Distinct circadian time structures characterize myeloid and erythroid progenitor and multipotential cell clonogenicity as well as marrow precursor proliferation dynamics", *Experimental Hematology*, 26:523-533 (1998).

Zanello, S., et al., "Expression of the circadian clock genes clock and period1 in human skin", *J. Invest. Dermatol.*, 115:757-760 (2000).

Zimmermann, F., et al., "The sensitivity of in vitro erythropoietic progenitor cells to different erythropoietin reagents during development and the role of cell death in culture", *Exp. Hematol.*, 24(2):330-339 (1996). [Abstract Only].

\* cited by examiner

COLONY ASSAY MINIATURIZATION WITH ENUMERATION OUTPUT

CROSS-REFERENCE TO RELATED APPLICATIONS

This application claims priority from U.S. Provisional Patent Application Ser. No. 60/942,966, filed Jun. 8, 2007. This application is a continuation-in-part of U.S. patent application Ser. No. 12/049,921, filed Mar. 17, 2008, now U.S. Pat. No. 7,883,861, which is a continuation of U.S. patent application Ser. No. 10/645,077, filed Aug. 21, 2003, issued as U.S. Pat. No. 7,354,730, which is a continuation-in-part of U.S. patent application Ser. No. 10/059,521, filed Jan. 29, 2002, issued as U.S. Pat. No. 7,354,729. U.S. patent application Ser. No. 10/059,521 filed Jan. 29, 2002, claims the benefit of the filing date of U.S. Provisional Patent Application Ser. No. 60/264,796, filed Jan. 29, 2001. This application is also a continuation-in-part of U.S. patent application Ser. No. 12/049,815, filed Mar. 17, 2008, now U.S. Pat. No. 7,700,354, which is a divisional of U.S. patent application Ser. No. 10/059,521, filed Jan. 29, 2002, issued as U.S. Pat. No. 7,354,729. Each of these applications is hereby incorporated by reference in its entirety.

FIELD OF THE INVENTION

The present invention relates generally to high-throughput assays, kits, and methods for determining both proliferation and differentiation of lympho-hematopoietic stem cells and progenitor cells in a single assay. The present invention relates generally to high-throughput assays, kits, and methods for determining cell potency lympho-hematopoietic stem cells and progenitor cells in a single assay.

BACKGROUND

Hematopoietic stem cell transplantation (HSCT) would benefit from assays to ensure that the processed cells to be transplanted into a patient will home to the designated target organ, engraft or seed in that organ, initiate proliferation, and finally, reconstitute or repopulate the organ or tissue. Regardless of the cell source (bone marrow, mobilized peripheral blood, umbilical cord blood) and the type of transplantation performed (autologous or allogeneic), it is desirable to ensure the quality of the stem cells transplanted because, patients receiving the stem cell infusion have generally had their hematopoietic system partially or totally ablated by radiation and cytotoxic drugs and are at increased risk of dying if the transplanted cells do not engraft and repopulate their hematopoietic system. The first human autologous bone marrow transplantation (BMT) was performed by Kurnick et al. in 1958. Kurnick and Robinson, Colony growth of human peripheral white blood cells in vitro, Blood 37: 136 (1971). No assays to determine the quality of human transplanted cells with respect to their growth and engraftment potential were available until Pike and Robinson in 1971 applied the in vitro colony forming assays, first published in 1966, to human cells. Pike and Robinson, Human bone marrow colony growth in agar-gel, J Cell Physiol, 76: 77-84 (1970). Bradley and Metcalf, The growth of mouse bone marrow cells in vitro, Aust J Exp Biol Med, 44: 287 (1966).

The colony forming cell (CFC) assay (CFCA), first published in 1966 is a functional assay to detect morphologically unidentifiable stem and progenitor cells of the blood-forming (hematopoietic) tissue, because they are so few in number. The assay allows these cells to be stimulated in the presence of growth factors and cytokines and to undergo proliferation and division so that the daughter cells can differentiate into morphologically recognizable mature cells. This functional ability is detected by allowing the cells to grow in an immobilizing, semi-solid medium such as methylcellulose. As the cells divide, they remain in place and form a colony of cells that can be identified morphologically under an inverted microscope. Thus, even though the original cells that produce a colony cannot be identified morphologically, their functional ability to produce a colony can be detected and, therefore, by inference, their presence can be detected.

Despite the fact that the CFCA has been available for over 40 years, the technique has undergone few changes. The ability to detect multiple cell populations, however, even from the lymphopoietic system, has been established. The incorporation of recombinant growth factors and cytokines was introduced in the 1980s and 1990s as was the ability to culture the cells under low serum or serum-free conditions. Even with these additions, the assay has remained highly subjective due to the requirement to manually enumerate both the number and types of colonies produced. The subjectivity of the assay also means that the assay is extremely difficult to validate between different laboratories or even within a single laboratory due to the wide variation in what different individuals consider to be one type of colony versus another. Since there is no external parameter, such as a biochemical entity or process, to which the results can be compared, the CFCA assay has never been standardized. Regardless of the application for which the CFCA is used, there is no ability to compare the results of experiments or studies either within or between laboratories. As a result, if the CFCA is used as an end-point assay to control a particular procedure or process, for example, during the production of a stem cell product for transplantation into a patient, it is impossible for laboratories around the world to compare their results because of the non-standardized manner in which the colonies are manually enumerated. The result is that regulatory agencies have never been able to define specific criteria by which a procedure or process using the colony forming cell assay should be performed or the applicable range of results that should be acceptable.

The cell processing laboratory (CPL) is responsible for a quality product that is directly related to the success of the stem cell transplant. To this end, standards to maintain and enhance the quality and safety of the transplantation process through inspection and accreditation have been controlled by two groups in the United States, namely the American Association of Blood Banks (AABB) and Foundation for the Accreditation of Cellular Therapy (FACT), and in Europe by the Joint Accreditation Committee of ISCT-Europe and EBMT (JACIE). The U.S. Food and Drug Administration (FDA) has provided guidelines, especially since the implementation of gene therapy and ex vivo hematopoietic stem cell expansion protocols.

However, standards both the U.S. and Europe for ensuring that sufficient numbers of viable stem cells exhibiting proliferative or growth potential are distinctly lacking in information. There are two primary reasons for this. First, the absence of standardized, robust, and non-subjective assays, and second, a lack of consensus regarding the procedure or procedures to be used. For example, the JACIE standards state in Section D4.270, "For products undergoing manipulation that alters the final cell population, a relevant and validated assay, where available, should be employed for evaluation of the target cell population before and after the processing procedure(s)". The Joint Accreditation Committee of ISCT-Europe and EBMT, Standards for hematopoietic progenitor cell collection, processing and transplantation (2003). Many transplant centers and umbilical cord blood storage facilities routinely perform colony-forming assays for quality control purposes and clinical monitoring in a stem cell transplantation setting. However, their use has been called into question. In an article by Henon et al. in 2001, the authors state, "Determination of the graft content in CFU-GM was the only one available until the end of the eighties. But, for technical reasons, and also because it does not actually evaluate the self-renewal potential of the cell products reinfused, it has now been commonly replaced by the determination of CD34+ cell amounts, which are known to contain the pluripotent hematopoietic stem cells." Henon, et al., Importance of CD34+ cell subsets in autologous PBSC transplantation: The mulhouse experience using CD34+, J Biol Regul. Homeost. Agents, 15: 62-67 (2001).

Despite the availability of in vitro assays to detect stem cells with different degrees of "sternness" or primitiveness and, therefore, different degrees of self-renewal potential, the colony-forming assays suffer from many drawbacks. The assays are time-consuming to perform and require a high degree of technical expertise to manually enumerate and differentiate colonies. The assay is highly subjective and there is a lack of standardization in procedure, performance, and colony enumeration. From a scientific viewpoint, the most important parameter to ascertain is not whether the cells can differentiate but whether they can proliferate, since once proliferation is underway, differentiation invariably follows. Therefore, assessing the differentiation capability of cells, as detected in the colony-forming assay, is secondary to their ability to initiate and sustain proliferation.

SUMMARY

A system combining a clonogenic differentiation assay with an instrument-based ATP bioluminescence proliferation assay to produce a standardized colony-forming stem and progenitor cell potency assay is provided.

High-throughput assays, kits, and methods for determining both proliferation and differentiation of lympho-hematopoietic stem cells and progenitor cells in a single assay are provided.

A standardized colony forming cell assay for determining both proliferation and differentiation of lympho-hematopoietic stem cells and progenitor cells in a single assay is provided.

Provided is a method for determining both proliferation and differentiation in a population of primitive lympho-hematopoietic cells, the method comprising the steps of incubating a cell population comprising primitive lympho-hematopoietic cells in a cell growth medium comprising fetal bovine serum having a concentration of between 0% and about 30%, methyl cellulose having a concentration of between about 0.4% and about 0.7%, and in an atmosphere having between about 3.5% oxygen and about 7.5% oxygen; counting colonies formed from the cell population of primitive lympho-hematopoietic cells; contacting the cell population with a reagent capable of reacting with ATP and generating luminescence in the presence of ATP; detecting luminescence generated by the reagent that reacted with the ATP in the cell population, the level of luminescence indicating the amount of ATP in the cell population, wherein the amount of ATP indicates the proliferative status of the primitive hematopoietic cells; and correlating the number of colonies formed from the cell population of primitive lympho-hematopoietic cells with the amount of ATP detected.

BRIEF DESCRIPTION OF THE FIGURES

FIG. 6 shows a comparison of the results of detecting the human multipotential stem cell population (CFC-GEMM) as a function of plated cell concentration using various assays including (a) HALO®-96 MeC performed at 7 days, (b) CAMEO™-4 performed by manual enumeration at 14 days, and (c) CAMEO™-96 performed by initially counting colonies by manual enumeration followed by an ATP assay (labeled as HALO-14 days) on the same samples, both at 14 days.

FIG. 7 shows the total number of colonies per well plotted against the mean ATP production per well in two types of colony forming cell assays, illustrating the correlation between results obtained from the from the 4-well assays (CAMEO™-4) and the 96-well assays (CAMEO™-96).

DETAILED DESCRIPTION OF THE PREFERRED EMBODIMENTS

Figure 1:
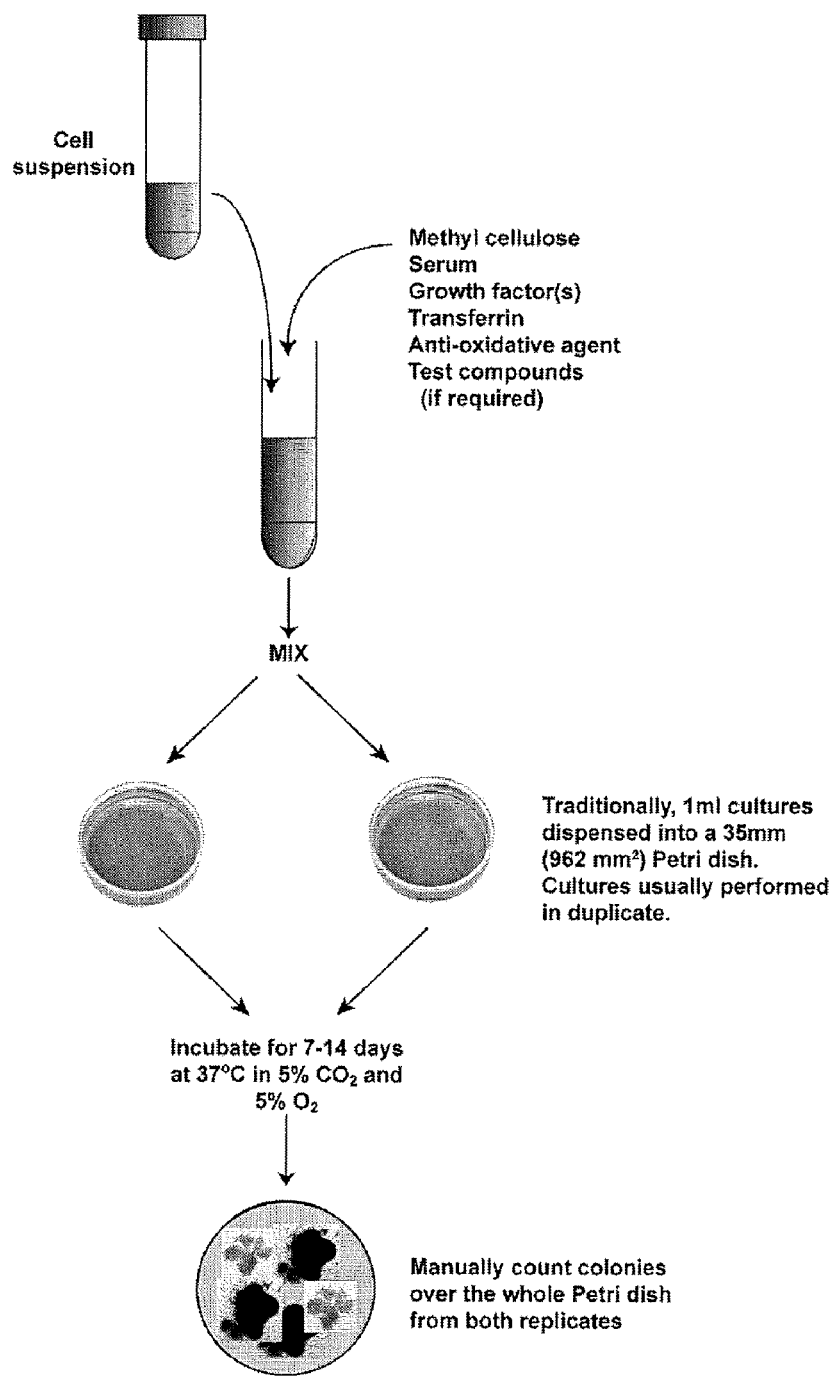
FIG. 1 is a schematic diagram of a traditional colony forming assay.

The colony assay miniaturization with enumeration output (CAMEO™) platform combines a clonogenic differentiation assay with an instrument-based ATP bioluminescence proliferation assay to produce a standardized colony-forming stem and progenitor cell potency assay.

HALO® refers Hematopoietic and/or Hematotoxicity Assays via Luminescence Output. The HALO® platform was developed as a high throughput assay of hematopoietic stem and progenitor cell proliferation and is described in greater detail in U.S. Pat. Nos. 7,354,729 and 7,354,730. In one embodiment, HALO® is a modified methyl cellulose colony-forming-based assay, but instead of detecting differentiation capability after 14 days of incubation, it directly measures proliferative potential of cells after only 7 days of incubation. (The HALO® platform is further described in U.S. Pat. Nos. 7,354,729 and 7,354,730, and co-pending U.S. patent application Ser. No. 11/561,133, each incorporated herein by reference in its entirety.) As cells proliferate, there is a proportional increase in intracellular ATP concentration. After the incubation period, the intracellular ATP is released from the cells by lysis. The released ATP then drives a luciferin/luciferase reaction to produce bioluminescence in the form of light which can be detected and measured non-subjectively in a plate luminometer. By measuring intracellular ATP, the assay can be standardized. A 96-well plate format allows for versatility, flexibility, and rapid, automated production of reproducible results from large numbers of samples.

The HALO® platform was originally developed for biotechnology and pharmaceutical companies to examine the effects of compounds on multiple lympho-hematopoietic populations from multiple species simultaneously in a high-throughput manner. The further develop the CAMEO™ platform allows a more rapid, standardized, and non-subjective quality control assay than the traditional colony-forming assay; the demonstration that cells processed for transplantation purposes exhibit proliferative (growth) potential; effective prediction of long- and short-term engraftment; and effective prediction of long- and short-term balanced, multi-lineage reconstitution.

The HALO® assay has been designed so that components, in the form of premixed reagents, are added in specific ratios to one or more cell suspensions, and plated in as many replicates as required, into a 96-well plate, for example. During the incubation period, the cells, stimulated by growth factor and/or cytokine combinations (proliferation agents), proliferate and divide. Depending on the cell population to be detected and the species used, clusters of cells begin to form in the semi-solid methyl cellulose that is used to immobilize the cells. Some, or perhaps all, of these clusters, will eventually form colonies of differentiated cells, and these are usually counted manually under a microscope in the classical colony-forming assay. Whether these clusters form large or small mature colonies of differentiated cells is dependent on the proliferative and functional capability of the colony-forming cell being tested. If not left to mature into colonies, these clusters or "proliferation units" contain proliferating cells all of which are producing ATP. At a time when proliferation is increasing, the cells in the culture are lysed to release ATP into the surrounding medium. After a short incubation time (about 10 minutes), the amount of ATP released is determined by its reaction with luciferin in the presence of the enzyme luciferase. The reaction is as follows:

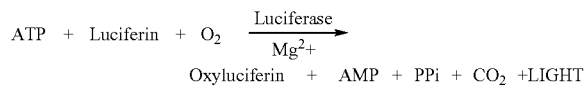

The bioluminescence emitted is detected and measured in a plate luminometer as relative luminescence units (RLU). To standardize the assay, an ATP standard is provided. An ATP dose response curve is performed with the assay and allows conversion of RLU to be expressed in standardized (molar) units of ATP. This allows for experiments, performed at different times and in different locations, to be compared.

Due to its versatility and ease of use, the HALOS platform has been developed to meet a wide variety of applications. One such development from the HALO® platform is the CAMEO™ assay platform. In general terms, there are four basic steps involved in performing assays using the CAMEO™ platform. First is cell preparation in which cells are prepared according to a user-defined or pre-validated protocol. After determining the cell count, the cells are preferably adjusted to a specific cell concentration. The second step is cell culture. The cell solution is added to each tube containing the pre-mixed culture reagents of the assay for each cell population to be detected. The contents of the tubes are mixed and cells and cell culture media are dispensed into pre-defined wells of a 96-well plate. The cultures are incubated for 14 days at 37° C. in a fully humidified atmosphere containing 5% $CO_2$ and, if possible, 5% $O_2$. The third step is to count the colonies. The fourth step is the measurement of proliferative or growth potential by luminescence. To measure bioluminescence, intracellular ATP, produced as the cells proliferate, is released by the addition of an ATP-lysing and monitoring reagent (ATP-MR). After a short incubation period, the bioluminescence is measured in a plate luminometer. Prior to sample luminescence measurements, an ATP standard curve is preferably performed. The ATP standard curve has several purposes, including, to ensure that the reagents and luminometer are working correctly, to provide standardization for the assay, and to enable the conversion of RLUs to molar concentrations of ATP.

The procedure for a traditional colony forming cell assay is shown in FIG. 1. In the CFCA, a cell suspension is added to a mixture of components that are required for the cells to grow. These components generally include methyl cellulose, serum, growth factors, transferrin, an anti-oxidative agent, and optionally, test compounds. Once the cells have been added, all components are mixed together. In the original and commercial form of this assay, produced by such companies as Stem Cell Technologies, R & D Systems, and Sigma Chemical Company, a total volume of about 3 ml is used so that 1 ml can be dispensed into each of two 35 mm Petri dishes. This relatively large volume is required because the assay requires the use of methylcellulose, and the methylcellulose is viscous and tends to stick to the sides of the tube so that not all of the volume can be dispensed. In these assays, dispensing of the reagents is normally performed using a syringe and needle.

Figure 2:
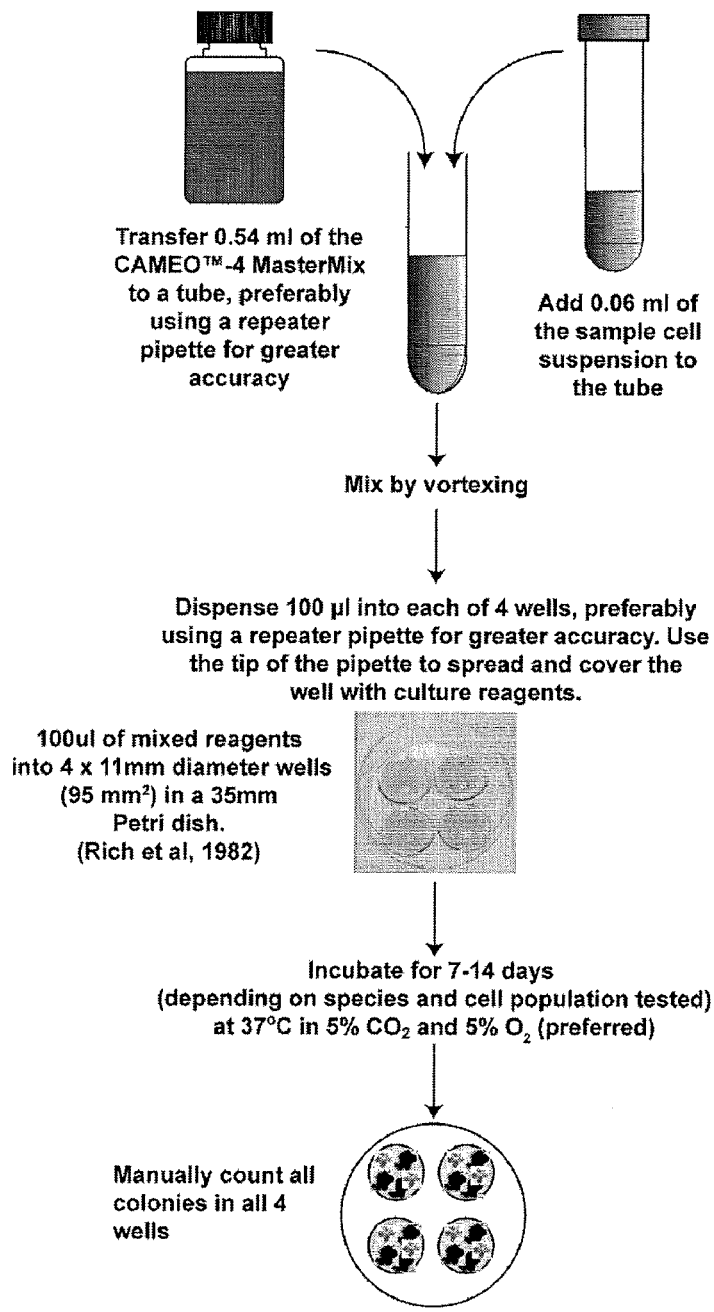
FIG. 2 is a schematic diagram of a miniaturized colony forming assay known as Colony Assay Miniaturization with Enumeration Output or CAMEO™-4.

In 1982, Rich and Kubanek published a miniaturized version of this assay. (Rich, I. N. and Kubanek, B., The effect of reduced oxygen tension on colony formation of erythropoietic cells in vitro, Br. J. Haematol., 52(4): 579-588 (1982)). In this smaller scale version, a 35 mm Petri dish with 4 small wells or rings was used. Instead of dispensing 1 ml of mixed components, only 100 µl of reagents is dispensed into each well. This smaller volume not only allows the reduction of required quantities of expensive reagents such as fetal bovine serum (FBS), growth factors, and cytokines, but also allows the assay to be performed in quadruplicate and the manual enumeration to be slightly faster than that in two 1 ml Petri dishes. This miniaturized assay is now referred to as CAMEO™-4 (Colony Assay Miniaturization with Enumeration Output). FIG. 2 shows a schematic view of the procedure to perform the CAMEO™-4 protocol. Compared to a traditional colony forming cell assay, the CAMEO™-4 protocol utilizes reduced volumes to perform the assay. Like the original CFCA, in the CAMEO™-4 platform, human cells are cultured for 12-14 days and animal cells are cultured for 7 days. Additionally, both assays also use manual enumeration of the colonies.

Figure 3:
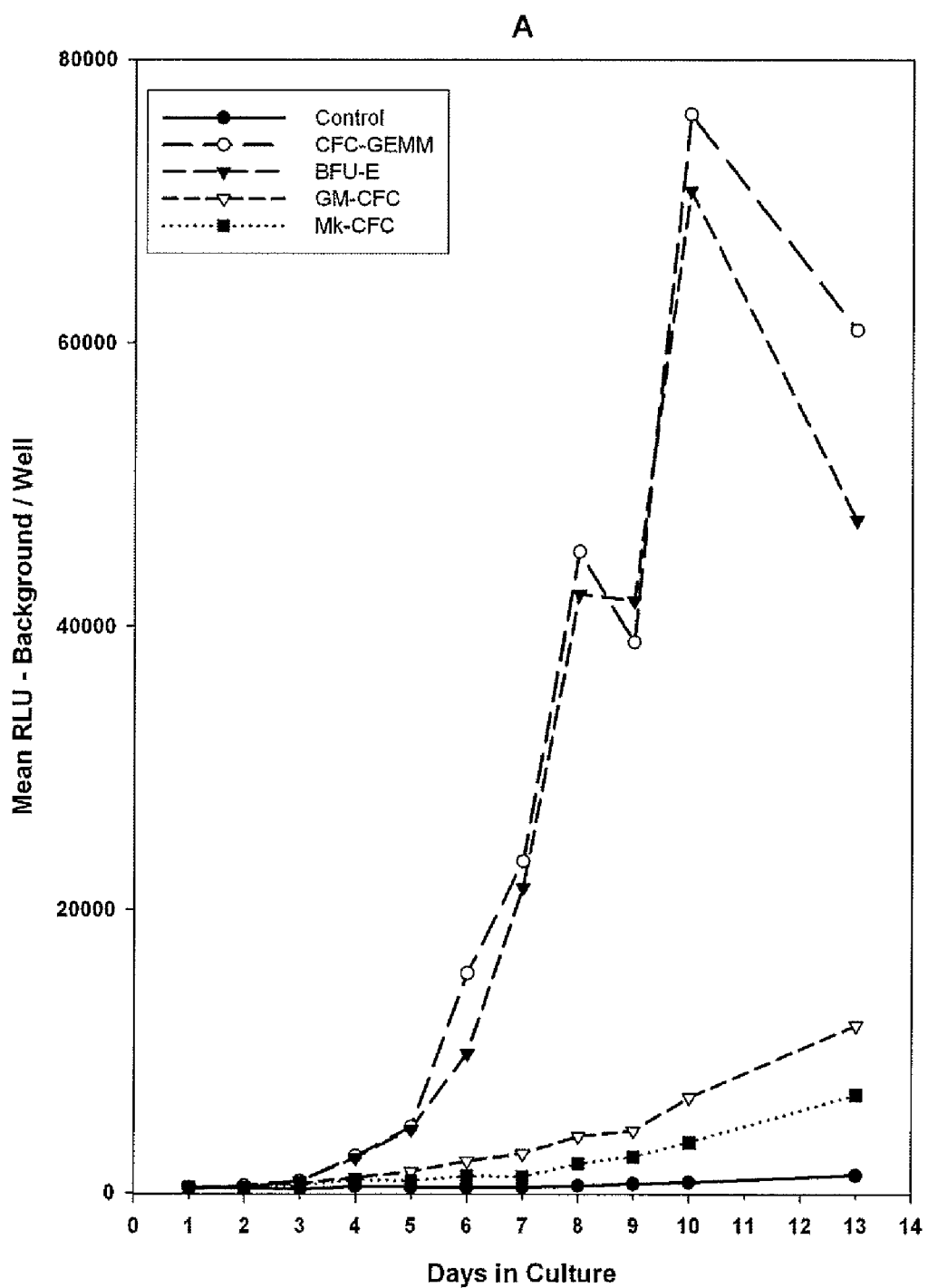
FIG. 3 is a graph showing the levels of intracellular adenosine triphosphate (iATP) over time in various lympho-hematopoietic cells grown in a methyl cellulose culture.

It has been demonstrated that the HALO® platform converted the CFCA from a differentiation assay into a proliferation assay. The proliferation kinetics of lympho-hematopoietic cell growth in methyl cellulose is such that at 5 or 7 days, the time point at which intracellular adenosine triphosphate (iATP) was measured as a function of proliferation for animal or human cells, respectively, little or no differentiation had occurred. The time course indicated that even though the iATP concentration increased exponentially after these time periods, it was accompanied by differentiation of the cells and continued growth of the cells into colonies of functionally mature cells. The iATP concentration increased until about day 10 of culture and then, for most cell populations detected, decreased. The levels of iATP over time in various lympho-hematopoietic cells grown in a methyl cellulose culture are shown in FIG. 3. The decrease in iATP after about 10 days in culture is a result of the differentiation process taking over from the proliferation process. Although some cells are still proliferating within the colonies after 10 days in culture, there are few that are capable of proliferating because most have undergone differentiation and have discontinued their proliferation program.

Figure 4:
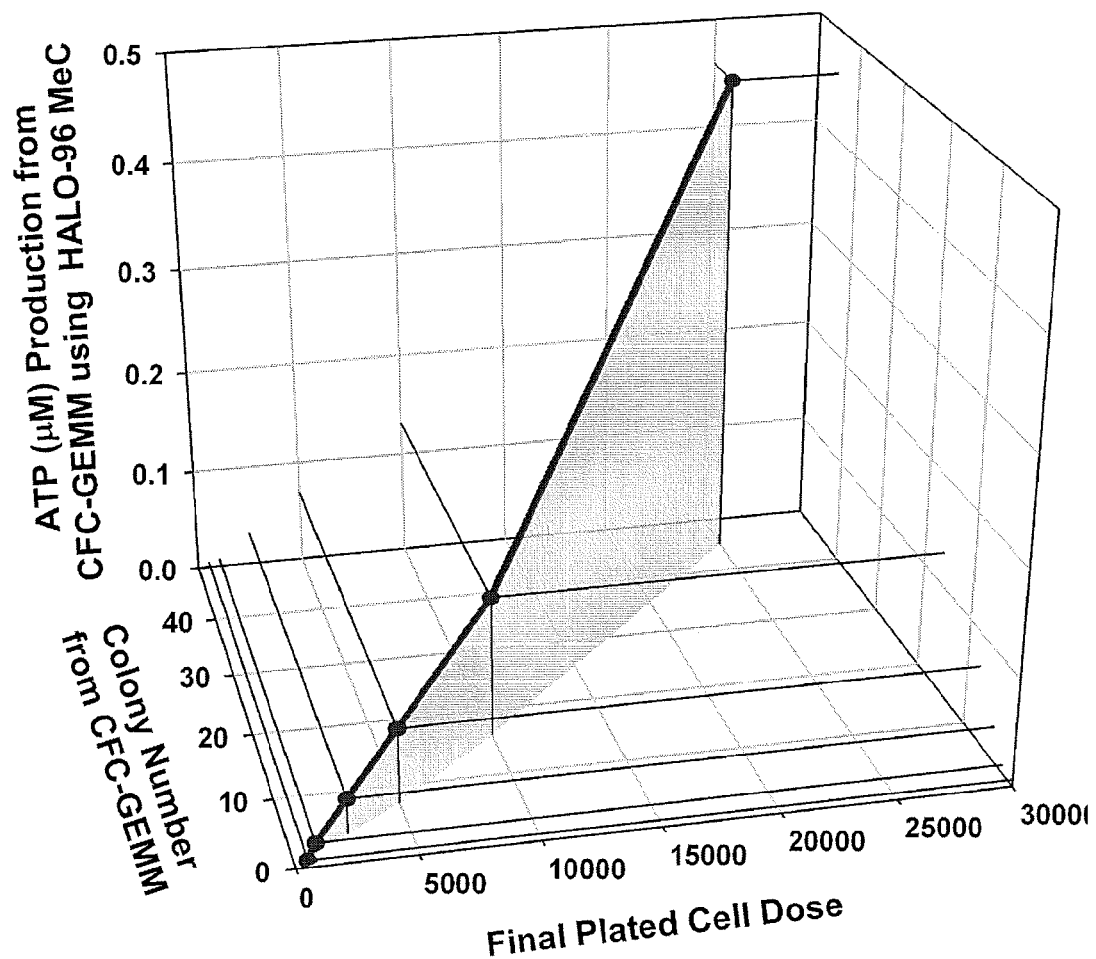
FIG. 4 is a 3 dimensional graph showing the correlation between the number of cells plated per well, the number of colonies generated using a traditional colony forming assay, and the mean ATP production per well for the human multipotential stem cell population, CFC-GEMM.

A correlation has also been demonstrated between the number of cells plated per well, the number of colonies generated using a traditional colony forming assay, and the mean ATP production per well for the human multipotential stem cell population, CFC-GEMM. This correlation is illustrated in the 3 dimensional graph in FIG. 4. As seen in FIG. 4, mean ATP production per well for the human multipotential stem cell population (CFC-GEMM) detected on day 7 is plotted against the total number of colonies manually enumerated on day 14 (performed in a separate, but parallel assay) as a function of the cell concentrated plated per well. While ATP production was measured using a HALO® assay performed in a 96-well plate at day 7, and the number of colonies were counted using what is now called CAMEO™-4, these assays used exactly the same reagents and were cultured under exactly the same conditions. The consequence of the correlation obtained is, therefore, that colony counts can now be expressed as ATP concentration equivalents. In other words, because HALO® is standardized against an external ATP standard, if the CFCA and HALO® assays are performed under exactly the same conditions, the CFCA can now be standardized against HALO®.

CAMEO™, or the colony assay miniaturization with enumeration output assay provides a standardized colony forming cell assay. It has been shown that if both the CFCA and HALO® are performed in the same 96-well plate format under exactly the same conditions, and the cultures incubated for 14 days (rather than the 7 days usually used for the HALOS assay), the CFCA can be fully standardized. The CAMEO™ platform provides an assay that measures both proliferation and differentiation simultaneously in a single assay, providing at least twice as much information from a single assay is provided. A colony forming cell assay that can be standardized against an external, independent biochemical marker is provided. With a standardized colony forming cell assay, procedures that depend on the outcome of the assay can be controlled and standardized. Standardization of the colony forming cell assay also means that results can be compared and validated within and between different laboratories, and the assay can be subjected to proficiency testing and, therefore, can be regulated by agencies.

Figure 5:
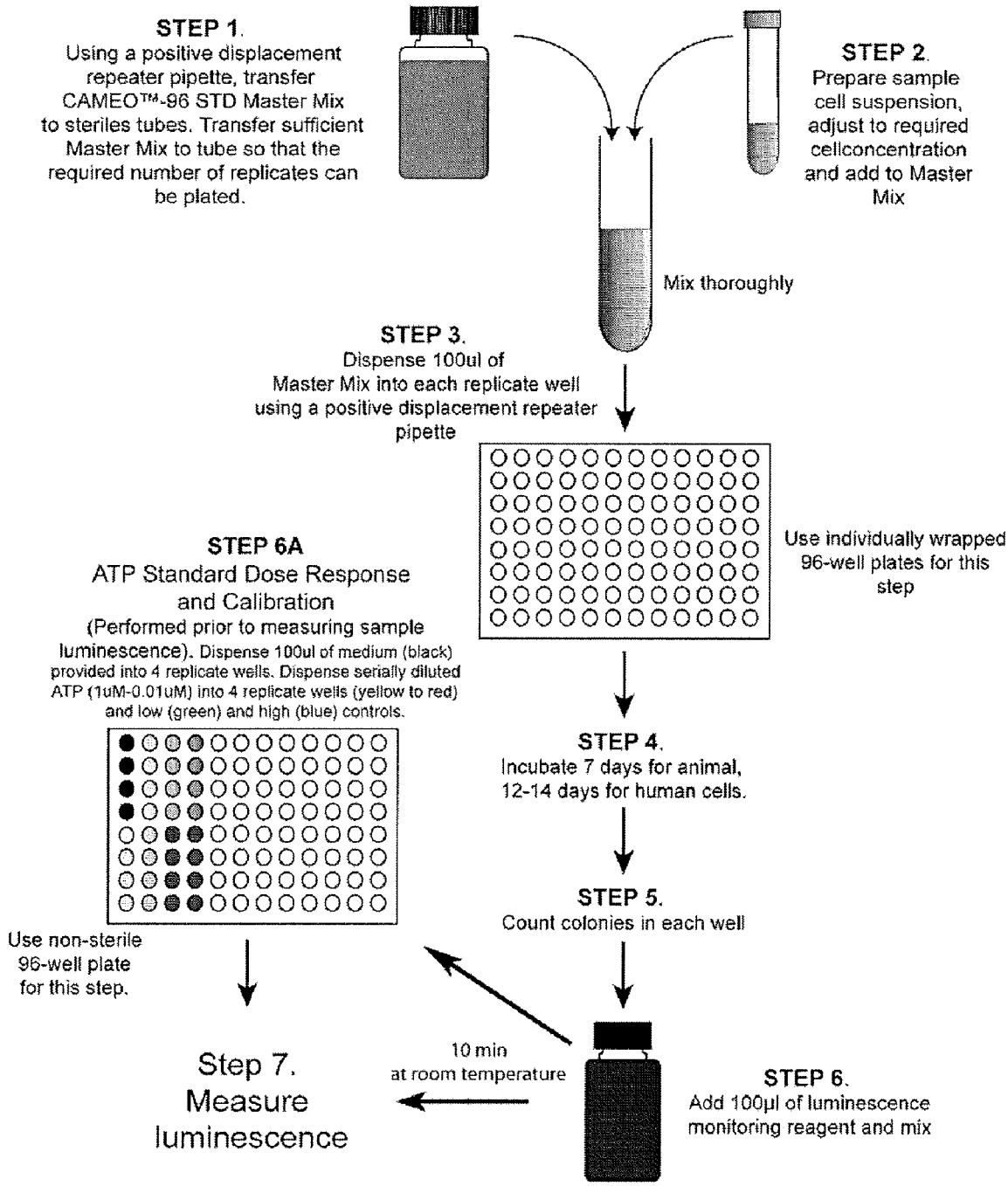
FIG. 5 is a schematic diagram of a Colony Assay Miniaturization with Enumeration Output, or CAMEO™-96.

The CAMEO™ assay is performed as follows and as shown in FIG. 5. First, the cell suspension, at 10 times the final cell required concentration, is added to a specific volume of CAMEO™-96 master mix containing the same components as the HALO®-96 MeC master mix (described in greater detail below and in U.S. Pat. Nos. 7,354,729 and 7,354,730). The "master mix" refers to a mixture of three reagents including methyl cellulose, proliferation agents, and serum, which may be pre-mixed and dispensed into individual tubes for each of the cell populations to be tested. A proliferation agent is defined as comprising one or more growth factors, one or more cytokines, or combinations thereof. The proliferation agent or agents are also referred to as "growth factor mix" in the context of describing the kit components. The volume of the master mix will depend on the number of replicate wells required. For example, if 6 replicate wells are required for each sample, then 100 µl of cell suspension is added to 900 µl of Master Mix to produce a final volume of 1 ml.

Preferably by using an electronic positive displacement repeater pipette, 100 µl of the Master Mix is dispensed into each of the replicate wells in a 96-well white-walled, transparent bottom plate. The plate is then transferred to an incubator, and the cells are cultured for 7 days for animal cells and 14 days for human cells at 37° C. in a fully humidified atmosphere containing 5% $CO_2$ and, where possible, 5% $O_2$.

After the incubation period has elapsed, the plate is removed from the incubator, and the colonies are first counted manually under an inverted microscope. After counting the colonies, in order to differentiate the colony types, if desired, the plate can then be processed to determine the intracellular ATP concentration. This is performed by adding 100 µl of the ATP Monitoring Reagent to each well using either a multi-channel pipette (preferably electronic) or a liquid handler and then mixing. This procedure is exactly the same as the procedure for the HALO®-96 MeC assays as described in the pending U.S. patent applications cited above. After the addition of the ATP Monitoring Reagent, the plate is incubated for 10 minutes at room temperature. During this time, the cells are lyzed, and the bioluminescence reaction takes place.

Prior to measuring the experimental samples, an ATP standard dose response is performed as described for the HALO®-96 MeC platform. The 96-well plate containing the samples to be analyzed is then transferred to the plate luminometer and the ATP levels are measured. The luminometer software can be programmed to automatically convert the RLU (relative luminescence units) values into ATP concentrations from the ATP standard curve.

Thus, both the CFCA and HALO®-96 MeC are performed under the same conditions, and the results obtained at the same time.

EXAMPLES

Example 1

CAMEO Assay

The assay is performed in four general steps, including cell preparation, cell culture, counting of colonies, and luminescence measurement, as described below.

Step 1. Cell Preparation

The CAMEO™ assay kit can be used with peripheral blood (normal or mobilized), bone marrow or umbilical cord blood. Erythrocytes are first depleted from the cell populations as they can interfere with the assay when present at high concentrations.

Step 1A: Umbilical Cord Blood

Cord blood may be depleted of erythrocytes by using a Hetastarch® protocol or a density gradient separation so that, preferably, erythrocytes constitute less than 10% of the cell suspension. A small number of enucleated and nucleated erythrocytes present generally do not interfere with the assay. If it appears that erythrocytes are present in a high concentration, it is recommended that a micro method of density gradient centrifugation be performed.

Step 1B: Human, Non-Human Primate, or Canine Peripheral Blood, or Bone Marrow Cells A mononuclear cell (MNC) suspension is preferred for performing the CAMEO™ assay. A hematocrit of 10% or less is preferred to avoid interference of hemoglobin with the ATP analysis.

Step 1C: Isolation of Hematopoietic Subpopulations

Providing sufficient cells are available, subpopulations of stem and progenitor cells may be isolated and purified for use in the CAMEO™ assay. Magnetic cell isolation procedures are recommended, as these procedures allow rapid isolation of different cell populations with substantial purity, viability, and yield. Recommended cell concentrations for use in the CAMEO™ assays are shown in Table 1.

contents of each tube are thoroughly mixed using a vortex mixer. Cell suspensions are prepared as required. Table 1 shows the recommended cell concentrations for various cell types. The adjusted cell concentration is calculated for each sample accordingly. Table 2 shows the total volume of cell suspension used per a sample for various kit configurations. The total volume for the specific cell concentration to be used is prepared. The appropriate cell volumes are dispensed as shown in Table 2. For example, 100 μl in 0.900 ml of master mix or 125 μl in 1.125 ml of master mix. The contents of each tube are mixed thoroughly using a vortex mixer. To ensure that as little master mix as possible remains on the walls of the tube, the tubes are transferred to a centrifuge and spun up to 500 rpm. The centrifuge is turned off when the speed has reached 500 rpm. This concentrates the components but does

TABLE 1

Recommended Cell Concentrations for Different Cell Types, Cell Preparations and Cell States for the CAMEO ™-96 STD Platform

| Cell type | Cell preparation | Cell state | Working cell concentration (100 × Final Cell Concentration) | Final cell concentration per well |
|---|---|---|---|---|
| Bone marrow | MNC | Fresh/Frozen | $7.5 \times 10^4 - 5 \times 10^5$/ml | 750-5,000 cells/well |
| Peripheral blood | MNC | Fresh/Frozen | $1-5 \times 10^5$/ml | 1,000-5,000 cells/well |
| Umbilical cord blood | MNC | Fresh/Frozen | $7.5 \times 10^4 - 5 \times 10^5$/ml | 750-5,000 cells/well |
| Bone marrow | $CD34^+$ | Fresh/Frozen | $1-5 \times 10^4$/ml | 100-500 cells/well |
| Peripheral blood, mobilized | $CD34^+$ | Fresh/Frozen | $1-5 \times 10^4$/ml | 100-500 cells/well* |
| Umbilical cord blood | $CD34^+$ | Fresh/Frozen | $5 \times 10^3$/ml - $5 \times 10^4$/ml | 50-500/well |

Step 1D: Cell Viability and Concentration Adjustment

Viability is measured using trypan blue and a hemacytometer or by flow cytometry using 7-AAD or another vital stain. A viability of 85% or greater is recommended. Cell concentration is determined using either a hemacytometer or electronic cell/particle counter. The cell count is adjusted according to the preferred cell concentrations shown in Table 1. Note that the working cell concentration per ml is 100× the final cell concentration per well.

Step 2: CAMEO™ Cell Culture

The CAMEO™-96 assay kit contains a "master mix" of three reagents including methyl cellulose, proliferation agents (also referred to as "growth factor mix"), and serum pre-mixed and dispensed into individual tubes for each of the cell populations to be tested. The combination of methyl cellulose, proliferation agents, and serum components is referred to as the "master mix." By premixing all other components of the assay, only the cells need to be added. This allows the assay to be performed rapidly and with a minimum of manipulation.

Step 2A: Cell Culture

The frozen pre-mixed tubes are transferred to a 37° C. incubator or allowed to thaw at room temperature. Cells are not added before thawing is complete. When thawed, the not spin down the cells. Alternatively, the tubes may be allowed to stand for 3 to 5 minutes. The master mix culture including the master mix and cells is dispensed into the wells of a 96-well plate. A recommended plate configuration is shown below. To dispense master mix culture for each sample, a sterile 1.25 ml (or similar volume) syringe is attached to a repeater pipette with positive displacement, and 100 μl of the master mix culture is dispensed into the center of each of the replicate wells. For each sample, the repeater syringe is discarded and replaced with a new syringe. The culture plate is transferred to a 37° C., fully humidified incubator with an atmosphere of 5% $CO_2$. If possible, an incubator gassed with nitrogen to reduce the atmospheric oxygen concentration (21%) to 5% $O_2$ is used. Reducing the oxygen concentration helps increase the plating efficiency. Cells are incubated for 7 days. The 96-well plates have a transparent bottom; therefore, it is possible to observe cell growth at any time using an inverted microscope. Cell aggregates are counted prior to luminescence measurement.

The plate configuration may be determined by the number of replicates. For example, using a 96-well plate, six (6) replicates may be plated by row with replicates in positions 1 to 6 and 7-12 in each row. For eight (8) replicates, the replicates may be plated by column with replicates in positions A-H in each column.

TABLE 2

Cell Suspension Volumes

| No. of cell populations to be detected | Background Control included | No. of replicates | Volume of Master Mix per tube | Cell volume added to each tube | Total volume of cell suspension required/sample |
|---|---|---|---|---|---|
| 1 | No | 6 | 0.900 ml | 100 μl | 125 μl |
| 1 | No | 8 | 1.125 ml | 125 μl | 150 μl |
| 1 | Yes | 6 | 0.900 ml | 100 μl | 225 μl |

TABLE 2-continued

Cell Suspension Volumes

| No. of cell populations to be detected | Background Control included | No. of replicates | Volume of Master Mix per tube | Cell volume added to each tube | Total volume of cell suspension required/sample |
|---|---|---|---|---|---|
| 1 | Yes | 8 | 1.125 ml | 125 µl | 275 µl |
| 2 | No | 6 | 0.900 ml | 100 µl | 225 µl |
| 2 | No | 8 | 1.125 ml | 125 µl | 275 µl |
| 2 | Yes | 6 | 0.900 ml | 100 µl | 325 µl |
| 2 | Yes | 8 | 1.125 ml | 125 µl | 400 µl |
| 4 | No | 6 | 0.900 ml | 100 µl | 425 µl |
| 4 | No | 8 | 1.125 ml | 125 µl | 525 µl |
| 4 | Yes | 6 | 0.900 ml | 100 µl | 525 µl |
| 4 | Yes | 8 | 1.125 ml | 125 µl | 650 µl |
| 7 | Yes | 6 | 0.900 ml | 100 µl | 725 µl |

Step 3—Counting Colonies

Colonies are counted before measurement of luminescence measurement. The release of the intracellular ATP involves lysing the cells, therefore, counting the colonies is not possible after the luminescence measurement is performed.

Step 4—Luminescence Measurement

The ATP standard, controls, and reagents are allowed to reach room temperature before analysis. Unwrapped, non-sterile 96-well plates are used to perform the ATP standard dose response curve.

Step 4A: ATP Standard Dose Response

Five vials are prepared and labeled for the ATP dose response with the following ATP concentrations: vial 1: 1 µM; vial 2: 0.5 µM; vial 3: 0.1 µM; vial 4: 0.05 µM; and vial 5: 0.01 µM ATP. 900 µl of medium is added to vial 1. 300 µl of medium is added to vial 2. 900 µl of medium is added to vial 3. 900 µl of medium is added to vial 4. 900 µl of medium is added to vial 5. 100 µl of the supplied stock ATP solution (at 10 µM) is removed and transferred it to vial 1, and then mixed by vortexing. This ATP concentration is 1 µM.

300 µl from vial 1 is added to vial 2 and mixed, yielding a concentration of 0.5 µM. 100 µl from vial 2 is added to vial 4 and mixed, yielding a concentration of 0.05 µM. 100 µl from vial 1 is added to vial 3 and mixed, yielding a concentration of 0.1 µM. 100 µl from vial 3 is added to vial 5 and mixed, yielding a concentration of 0.01 µM.

100 µl of the supplied medium alone is added into wells A1, B1, C1 and D1 on the non-sterile luminescence plate. These wells are used to measure background luminescence. 100 µl from the ATP dilution in vial 5 is added to wells E1, F1, G1, and H1. 100 µl from the ATP dilution in vial 4 is added to wells A2, B2, C2, and D2. 100 µl from the ATP dilution in vial 3 is added to wells E2, F2, G2, and H2. 100 µl from the ATP dilution in vial 2 is added to wells A3, B3, C3, and D3. 100 µl from the ATP dilution in vial 1 is added to wells E3, F3, G3 and H3.

The required amount of ATP monitoring reagent (ATP-MR) is added to a non-sterile reagent reservoir. Using a multichannel pipette, 100 µl is added to the first column (A1-H1). Contents are mixed by repeated pipetting, and the tips are discarded. Tips are change for each new addition of ATP-MR. Well contents are mixed well.

100 µl of ATP-MR is added to each of the other columns, mixing the contents as described. This procedure is repeated for each column. The ATP plate is placed in the luminometer and timed for two minutes before initiating measurement.

Step 4B: Sample Measurement

The addition of ATP-MR is performed in the same manner as that for the ATP standard dose response curve. Preferably, the sample plate is placed in a humidified incubator set at 22-23° C. gassed with 5% $CO_2$ for 30 minutes to equilibrate or to reach room temperature. If only part of the plate has been used, the lid can be removed the lid and a sterile adhesive plate cover can be attached to the empty wells to avoid any contamination. Using a multichannel pipette (8- or 12-channels depending on the plate configuration), 100 µl of ATP-MR is added to the first column (A1-H1) or row (A1-12). The contents are mixed thoroughly. This procedure is repeated for each column or row using new tips. When the ATP-MR has been added to all wells, the cover is replaced and the plate is incubated for 10 minutes at room temperature to lyse the cells and stabilize the luminescence signal. When all of the sample wells have been treated, the plate is transferred to the luminometer and luminescence measurement is initiated. Results obtained from a luminometer are generally provided as Relative Luminescence Units (RLU). There is no standardization between luminometers. However, by performing an ATP standard dose response, the RLU values obtained can be converted into standardized ATP values.

Luminometers from different manufacturers vary. Depending on the method of luminescence measurement, the measurement parameters on the instrument may be set. These parameters are integration time and "gain". The integration time is set at 1 second. The "gain". is determined empirically and is generally performed when the ATP standard curve is measured. The gain is adjusted so that the percent coefficients of variation (% CV) for the mean of the replicates are the lowest possible values, generally about 5% or less. The measurement temperature of the instrument is set between 22° C. and 24° C. or turned off. Most luminometers are equipped with a plate shaking protocol, and it is not necessary to use the plate shaker mode.

Example 2

Assay and Kit Configurations

Various embodiments of the CAMEO™ assay have been designed for multiple configurations including, for example, single (mature) and dual (primitive and mature) stem cell assays, 4-population hematopoietic assays, 7-population lympho-hematopoietic assays, and primitive stem cell secondary re-plating assays. Specific applications include the following.

Example 2A

Single Stem Cell Potency Assay

The single stem cell potency assay detects and measures proliferation and differentiation potential of the multipotential stem cell population (CFC-GEMM).

Example 2B

Dual Stem Cell Potency Assay

The dual stem cell potency assay detects and measures the proliferation and differentiation potential of the primitive high proliferative potential stem and progenitor (HPP-SP) stem cell, which produces both lymphopoietic and hematopoietic lineages, and the mature CFC-GEMM population.

Example 2C

4-Population Potency Assay

The 4-population potency assay detects and measures proliferation and differentiation potential of CFC-GEMM, BFU-E, GM-CFC and Mk-CFC cell types.

Example 2D

7-Population Potency Assay

The 7-population potency assay detects and measures proliferation and differentiation potential of HPP-SP, CFC-GEMM, BFU-E, GM-CFC, Mk-CFC, T-CFC, B-CFC cell types and a background control.

Example 3

Assay and Kit Contents and Storage Conditions

TABLE 3

1 Plate Kit Contents CAMEO ™-96 STD

| Reagent | Contents | State shipped/State stored until use | No. of containers | Total Volume provided |
|---|---|---|---|---|
| Master Mix Tube | Methyl Cellulose/Growth Factor Mix/Serum Mix | Sterile, frozen/frozen | 16 | 0.900 ml each |
| Medium | IMDM | Sterile, frozen/frozen | 2 | 28 ml |
| ATP Standard | ATP | Frozen/Frozen | 2 | 220 μl each |
| ATP Controls | Bi-level ATP control | Frozen/Frozen | 4 sets of 2 | 0.425 ml each |
| Luminescence | ATP-Monitoring Reagent (ATP-MR)* | Frozen/Frozen | 2 | 12.0 ml each |
| Adhesive plate covering | — | — | — | 1 |
| 96-well plate | Sterile luminescence culture plates/non-sterile luminescence plate | 1 sterile/2 non-sterile | — | 3 |
| | Kit manual | — | — | 1 |

TABLE 4

2 Plate Kit Contents CAMEO ™-96 STD

| Reagent | Contents | State shipped/State stored until use | No. of containers | Total Volume provided |
|---|---|---|---|---|
| Master Mix Tube | Methyl Cellulose/Growth Factor Mix/Serum Mix | Sterile, frozen/frozen | 32 | 0.900 ml each |
| Medium | IMDM | Sterile, frozen/frozen | 4 | 56 ml |
| ATP Standard | ATP | Frozen/Frozen | 4 | 220 μl each |
| ATP Controls | Bi-level ATP control | Frozen/Frozen | 8 sets of 2 | 0.425 ml each |
| Luminescence | ATP-Monitoring Reagent (ATP-MR)* | Frozen/Frozen | 4 | 12.0 ml each |
| Adhesive plate covering | — | — | — | 2 |
| 96-well plate | Sterile luminescence culture plates/non-sterile luminescence plate | 2 sterile/3 non-sterile | — | 5 |
| | Kit manual | — | — | 1 |

TABLE 5

3 Plate Kit Contents CAMEO ™-96 STD

| Reagent | Contents | State shipped/State stored until use | No. of containers | Total Volume provided |
|---|---|---|---|---|
| Master Mix Tube | Methyl Cellulose/Growth Factor Mix/Serum Mix | Sterile, frozen/frozen | 48 | 0.900 ml each |

TABLE 5-continued

3 Plate Kit Contents CAMEO ™-96 STD

| Reagent | Contents | State shipped/State stored until use | No. of containers | Total Volume provided |
|---|---|---|---|---|
| Medium | IMDM | Sterile, frozen/frozen | 6 | 28 ml |
| ATP Standard | ATP | Frozen/Frozen | 6 | 220 µl each |
| ATP Controls | Bi-level ATP control | Frozen/Frozen | 12 sets of 2 | 0.425 ml each |
| Luminescence | ATP-Monitoring Reagent (ATP-MR)* | Frozen/Frozen | 6 | 12.0 ml each |
| Adhesive plate covering | — | — | — | 2 |
| 96-well plate | Sterile luminescence culture plates/non-sterile luminescence plate | 3 sterile/4 non-sterile | — | 7 |
|  | Kit manual | — | — | 1 |

TABLE 6

4 Plate Kit Contents CAMEO ™-96 STD

| Reagent | Contents | State shipped/State stored until use | No. of containers | Total Volume provided |
|---|---|---|---|---|
| Master Mix Tube | Methyl Cellulose/Growth Factor Mix/Serum Mix | Sterile, frozen/frozen | 64 | 0.900 ml each |
| Medium | IMDM | Sterile, frozen/frozen | 8 | 28 ml |
| ATP Standard | ATP | Frozen/Frozen | 8 | 220 µl each |
| ATP Controls | Bi-level ATP control | Frozen/Frozen | 16 sets of 2 | 0.425 ml each |
| Luminescence | ATP-Monitoring Reagent (ATP-MR)* | Frozen/Frozen | 8 | 12.0 ml each |
| Adhesive plate covering | — | — | — | 4 |
| 96-well plate | Sterile luminescence culture plates/non-sterile luminescence plate | 4 sterile/6 non-sterile | — | 10 |
|  | Kit manual | — | — | 1 |

Example 4

Proliferation Agents Used to Detect Various Cell Populations

Stem and progenitor cells are induced to proliferate and differentiate into lympho- and hematopoietic cell subpopulations by exposure to proliferation agents, including one or growth factors and/or cytokines. Table 7 shows examples of various combinations of growth factors and cytokines used to stimulate selected populations. Assays and kits specific for these call types are provided.

TABLE 7

Proliferation Agents for Selected Cell Populations

| Cell Population | Population abbreviation | Proliferation Agent (growth factors and cytokines) |
|---|---|---|
| High Proliferative Potential Stem and Progenitor Cells | HPP-SP "priming" | IL-3, IL-6, SCF, TP, Flt3L |
| High Proliferative Potential Stem and Progenitor Cells | HPP-SP "fully stimulated" | EPO, GM-CSF, G-CSF, IL-3, IL-6, SCF, TPO, Flt3L, IL-2, IL-7 |
| Colony-Forming Cell - Granulocyte, Erythroid Macrophage, Megakaryocyte | CFC-GEMM 1 | EPO, GM-CSF, G-CSF, IL-3, IL-6, SCF |
| Colony-Forming Cell - Granulocyte, Erythroid Macrophage, Megakaryocyte | CFC-GEMM 2 | EPO, GM-CSF, G-CSF, IL-3, IL-6, SCF, TPO |
| Colony-Forming Cell - Granulocyte, Erythroid Macrophage, Megakaryocyte | CFC-GEMM 3 | EPO, GM-CSF, G-CSF, IL-3, IL-6, SCF, TPO, Flt3L |
| Burst-Forming Unit-Erythroid | BFU-E 1 | EPO |
| Burst-Forming Unit-Erythroid | BFU-E 2 | EPO, IL-3, SCF |
| Colony-Forming Unit - Erythroid | CFU-E | EPO |
| Granulocyte-Macrophage Colony-Forming Unit | GM-CFC 1 | GM-CSF |
| Granulocyte-Macrophage Colony-Forming Unit | GM-CFC 2 | GM-CSF, IL-3, SCF |
| Granulocyte Colony-Forming Cell | G-CFC | G-CSF |
| Macrophage Colony-Forming Cell | M-CFC | M-CSF |
| Megakaryocyte Colony-Forming Cell | Mk-CFC | TPO, IL-3, SCF |
| T Cell Colony-Forming Cell | T-CFC | IL-2 |
| B Cell Colony-Forming Cell | B-CFC | IL-7 |

Example 5

Correlation of Total Colony Counts with ATP Production

Figure 6:
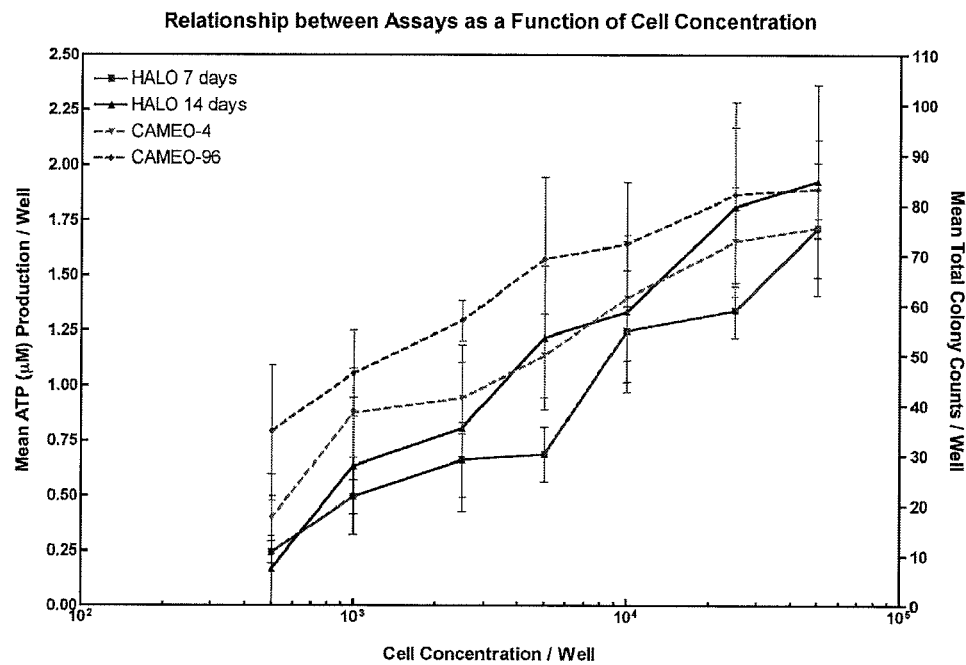
FIG. 6 is a graph showing the relationship between assays as a function of cell concentration.
Figure 7:
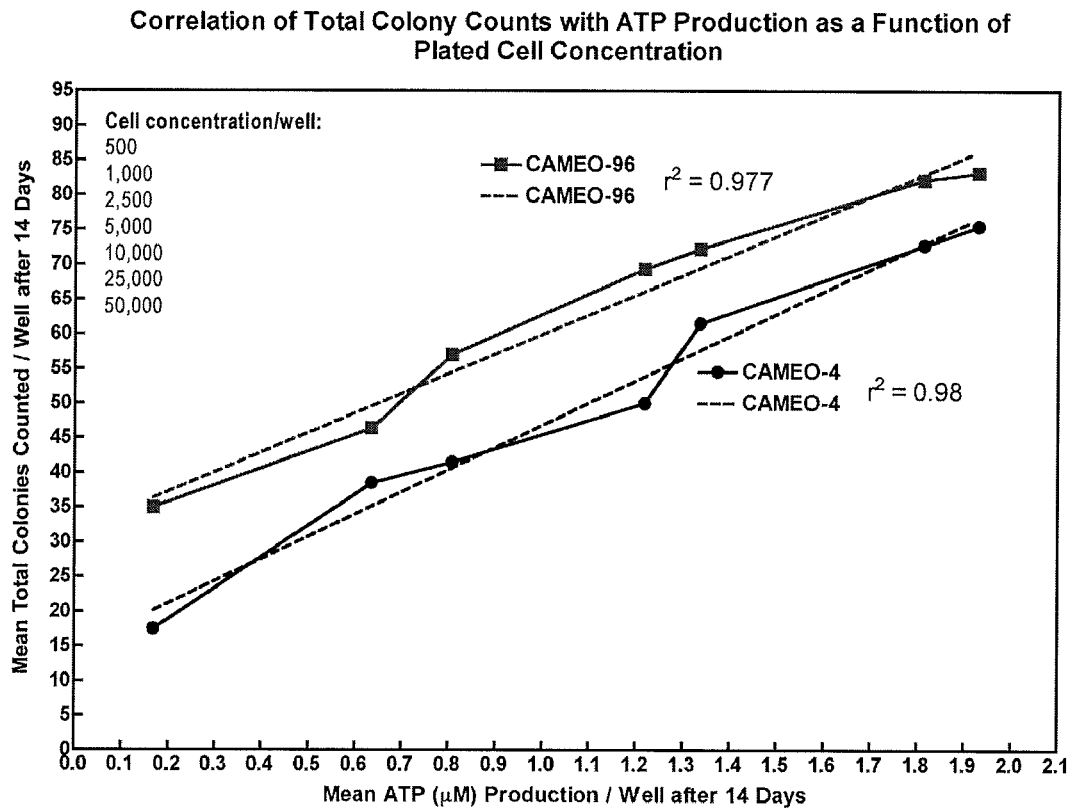
FIG. 7 is a graph showing the correlation of total colony counts with ATP production as a function of plated cell concentrations.

FIG. 6 is a graph of the relationship between assays as a function of cell concentration. FIG. 6 shows a comparison of the results of detecting the human multipotential stem cell population (CFC-GEMM) as a function of plated cell concentration using various assays including (a) HALO®96 MeC performed at 7 days, (b) CAMEO™-4 performed by manual enumeration at 14 days, and (c) CAMEO™-96 performed by initially counting colonies by manual enumeration followed by an ATP assay (labeled as HALO-14 days) on the same samples, both at 14 days. The results show parallel cell dose response curves. FIG. 7 is a graph showing the correlation of total colony counts with ATP production as a function of plated cell concentrations. FIG. 7 shows the total number of colonies per well plotted against the mean ATP production per well in two types of colony forming cell assays, the 4-well assays (CAMEO™-4) and the 96-well assays (CAMEO™-96). These results illustrate that a highly significant correlation is obtained, regardless of whether the CFCA is performed in 4 well plates (CAMEO™-4) or 96-well plates (CAMEO™-96).

Taken together, these results demonstrate that total colony counts obtained by manual enumeration can be expressed as ATP concentration equivalents. This allows for the standardization of the colony forming cell assay.

Example 6

Figure 8:
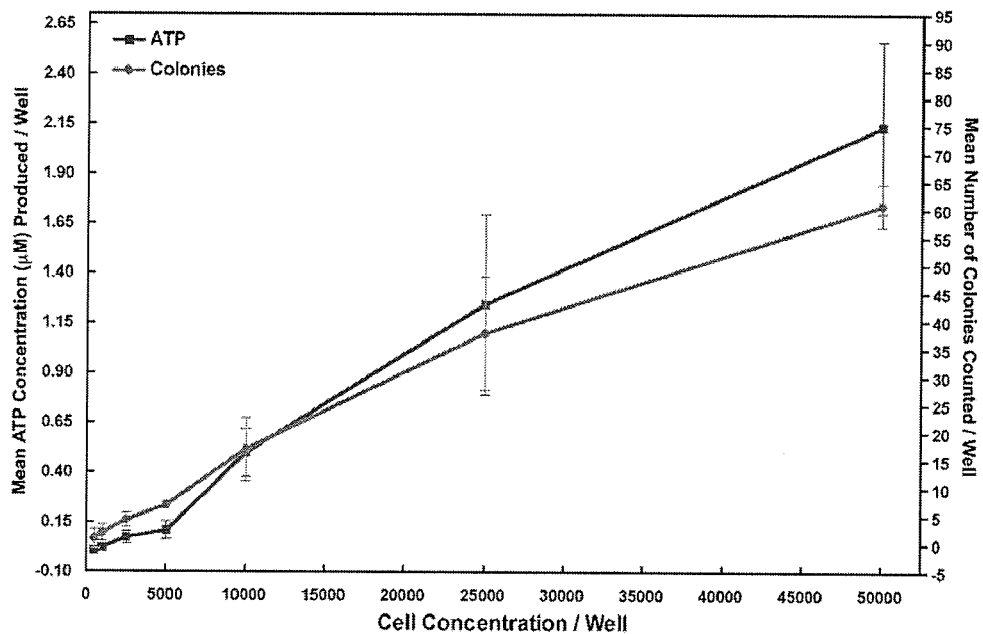
FIG. 8 is graph showing the relationship between the colony forming cell (CFC) differentiation assay and the bioluminescence ATP proliferation assay performed at 14 days for human CFC-GEMM.
Figure 9:
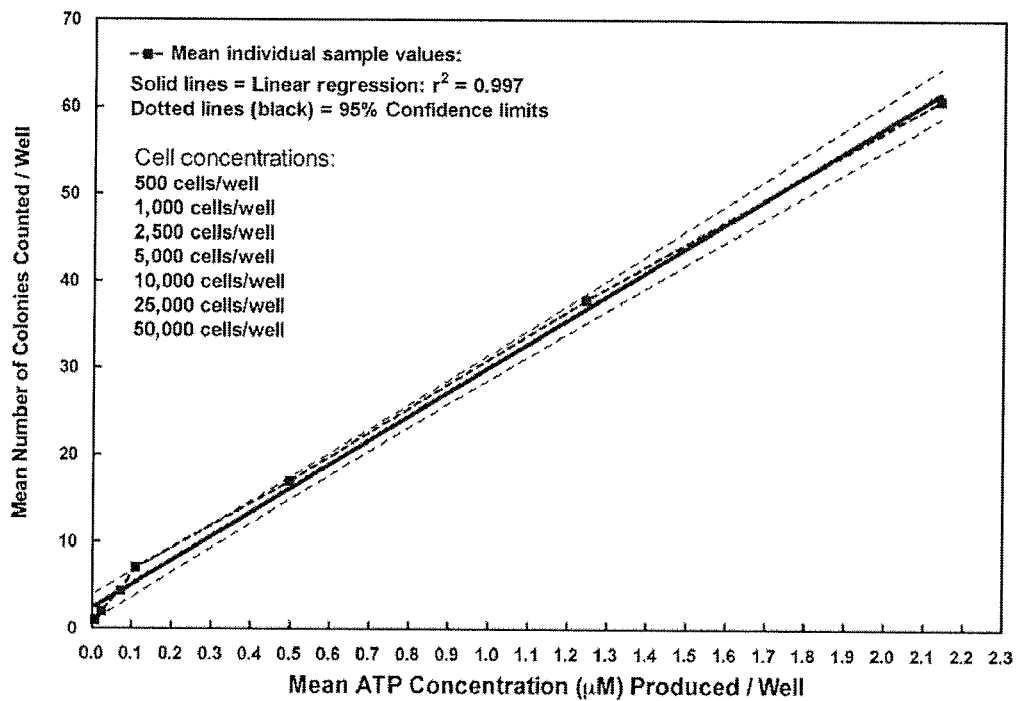
FIG. 9 is a graph showing the correlation between colony number counted and ATP production at 14 days for human CFC-GEMM.

Correlation Between Colony Number and ATP Production at 14 Days for Human CFC-GEMM FIG. 8 is graph showing the relationship between the colony forming cell (CFC) differentiation assay and the bioluminescence ATP proliferation assay performed at 14 days for human CFC-GEMM. FIG. 9 is a graph showing the correlation between colony number counted and ATP production at 14 days for human CFC-GEMM. The CAMEO™ assay allows for a direct comparison of the colony-forming cell assay with the HALO® bioluminescent assay, thereby validating the colony-forming cell assay with HALO®. This is correlation is evidenced by the straight line linear regression curve, as seen in FIG. 9. This shows that there is a direct correlation between the CFC assay and HALO®.

In summary, CAMEO™ platform provides an assay for blood-forming cells where both proliferation and differentiation can be measured in the same assay. This platform combines the elements of a traditional colony-forming assay and the HALO® assay. The CAMEO™ platform combines both a proliferation and a differentiation assay into one, yielding twice the amount of information from a single assay. Importantly, when a colony-forming assay and HALO® are performed under the same conditions, the two assays can be correlated. By performing an external ATP standard dose response for HALO®, the colony-forming assay is then standardized against HALO®. Therefore, this provides a means of standardizing the colony-forming assay which previously has not been possible. Based on this correlation, and by expressing the number of colonies produced in a CFCA in standardized ATP equivalents, the colony-forming assay can be validated, standardized, and compared within and between laboratories as has never been done before.

The invention claimed is:

1. A method for determining both the proliferation status and the differentiation status in a population of primitive lympho-hematopoietic cells, the method comprising the steps of:
   (a) providing a cell population comprising primitive lympho-hematopoietic cells;
   (b) incubating the population of primitive lympho-hematopoietic cells in a cell growth medium comprising fetal bovine serum having a concentration of between 0% and about 30%, methyl cellulose having a concentration of between about 0.4% and about 0.7%, and in an atmosphere having between about 3.5% oxygen and about 7.5% oxygen;
   (c) counting the number of colonies formed from the population of primitive lympho-hematopoietic cells, wherein the number of colonies formed indicates the differentiation status of the cell population of primitive lympho-hematopoietic cells;
   (d) contacting the population of primitive lympho-hematopoietic cells with a reagent capable of reacting with ATP and generating luminescence in the presence of ATP;
   (e) detecting luminescence generated by the reagent that reacted with the ATP in the population of primitive lympho-hematopoietic cells, the level of luminescence indicating the amount of ATP in the cell population, wherein the amount of ATP indicates the proliferative status of the primitive lympho-hematopoietic cells; and
   (f) correlating the number of colonies formed from the population of primitive lympho-hematopoietic cells with the amount of ATP detected from the population of primitive lympho-hematopoietic cells, thereby determining the proliferation status and the differentiation status of the population of primitive lympho-hematopoietic cells.

2. The method of claim 1, further comprising the step of contacting the population of primitive lympho-hematopoietic cells with a proliferation agent, the proliferation agent comprising one or more growth factors, one or more cytokines, or combinations thereof.

3. The method of claim 2, wherein the proliferation agent is selected from the group consisting of erythropoietin (EPO), granulocyte-macrophage colony stimulating factor (GM-CSF), granulocyte colony stimulating factor (G-CSF), interleukin-2 (IL-2), interleukin-3 (IL-3), interleukin-6 (IL-6), interleukin-7 (IL-7), stem cell factor (SCF), thrombopoietin (TPO), FMS-like tyrosine kinase 3 ligand (Flt3L), and combinations thereof.

4. The method of claim 2, wherein contacting the population of primitive lympho-hematopoietic cells with a proliferation agent generates a cell population substantially enriched in at least one hematopoietic stem cell lineage.

5. The method of claim 2, wherein contacting the population of primitive lympho-hematopoietic cells with a proliferation agent generates a cell population substantially enriched in at least one hematopoietic progenitor cell lineage.

6. The method of claim 1, wherein the concentration of fetal bovine serum is between about 0% and 10%.

7. The method of claim 1, wherein the concentration of methyl cellulose is about 0.7%.

8. The method of claim 1, wherein the concentration of oxygen in the atmosphere is about 5%.

9. The method of claim 1, wherein the population of primitive lympho-hematopoietic cells is isolated from an animal tissue selected from the group consisting of peripheral blood, bone marrow, and umbilical cord blood.

10. The method of claim 9, wherein the animal tissue is obtained from a human.

11. The method of claim 1, wherein the population of primitive lympho-hematopoietic cells comprises at least one lympho-hematopoietic progenitor cell lineage selected from the group consisting of high proliferative potential stem and progenitor cell (HPP-SP), colony-forming cell—granulocyte, erythroid macrophage, megakaryocyte (CFC-GEMM), burst-forming unit erythroid (BFU-E), colony-forming unit-erythroid (CFU-E), granulocyte-macrophage colony-forming cell (GM-CFC), granulocyte colony forming cell (G-CFC), macrophage colony-forming cell (M-CFC), megakaryocyte colony-forming cell (Mk-CFC), T cell colony-forming cell (T-CFC), and B cell colony-forming cell (B-CFC).

12. The method of claim 1, wherein the reagent capable of reacting with ATP and generating luminescence in the presence of ATP comprises luciferin and luciferase.

13. The method of claim 1, further comprising the step of identifying a population of primitive lympho-hematopoietic cells having a proliferative status suitable for transplantation into a recipient patient.

14. The method of claim 1, wherein between step (c) and step (d), the method further comprises: (c1) incubating the population of primitive lympho-hematopoietic cells for a period between about 5 days and about 14 days.

15. The method of claim 1, wherein between step (c) and step (d), the method further comprises: (c1) incubating the population of primitive lympho-hematopoietic cells for a period of about 5 days.

16. The method of claim 1, wherein between step (c) and step (d), the method further comprises: (c1) incubating the population of primitive lympho-hematopoietic cells for a period of about 7 days.

17. The method of claim 1, wherein between step (c) and step (d), the method further comprises: (c1) incubating the population of primitive lympho-hematopoietic cells for a period of about 10 days.

18. The method of claim 1, wherein between step (c) and step (d), the method further comprises: (c1) incubating the population of primitive lympho-hematopoietic cells for a period of about 12 days.

19. The method of claim 1, wherein between step (c) and step (d), the method further comprises: (c1) incubating the population of primitive lympho-hematopoietic cells for a period of about 14 days.

* * * * *